US008795308B2

(12) United States Patent
Valin

(10) Patent No.: US 8,795,308 B2
(45) Date of Patent: Aug. 5, 2014

(54) LAPAROSCOPIC GASTRIC AND INTESTINAL TROCAR

(76) Inventor: Elmer Valin, Woodbridge, CT (US)

( * ) Notice: Subject to any disclaimer, the term of this patent is extended or adjusted under 35 U.S.C. 154(b) by 1065 days.

(21) Appl. No.: 12/437,935

(22) Filed: May 8, 2009

(65) Prior Publication Data

US 2009/0281501 A1 Nov. 12, 2009

Related U.S. Application Data

(60) Provisional application No. 61/051,971, filed on May 9, 2008.

(51) Int. Cl.
*A61B 17/34* (2006.01)
*A61B 17/06* (2006.01)
*A61B 17/072* (2006.01)
*A61B 17/115* (2006.01)
*A61B 17/00* (2006.01)

(52) U.S. Cl.
CPC ....... *A61B 17/3417* (2013.01); *A61B 17/06066* (2013.01); *A61B 2017/0608* (2013.01); *A61B 17/072* (2013.01); *A61B 17/1155* (2013.01); *A61B 2017/00818* (2013.01)
USPC ............ 606/185; 606/167; 606/222; 606/223

(58) Field of Classification Search
CPC ..................... A61B 17/06066; A61B 17/3417; A61B 17/072; A61B 17/115; A61B 2017/0608; A61B 2017/00818; A61B 2017/1107; A61B 2017/1135; A61B 2017/1157; A61B 2017/1132
USPC .................. 606/184, 185, 222–227; 604/264; 227/175.1, 179.1, 180.1
See application file for complete search history.

(56) References Cited

U.S. PATENT DOCUMENTS

| | | | | | |
|---|---|---|---|---|---|
| 3,160,157 | A | * | 12/1964 | Chisman | 606/223 |
| 3,388,847 | A | * | 6/1968 | Kasulin et al. | 227/19 |
| 4,103,690 | A | * | 8/1978 | Harris | 607/128 |
| 4,699,142 | A | * | 10/1987 | Seal et al. | 606/223 |
| 4,957,502 | A | * | 9/1990 | Takase | 606/223 |
| 5,119,983 | A | * | 6/1992 | Green et al. | 227/179.1 |
| 5,205,459 | A | * | 4/1993 | Brinkerhoff et al. | 227/179.1 |
| 5,324,268 | A | * | 6/1994 | Yoon | 604/158 |
| 5,344,059 | A | * | 9/1994 | Green et al. | 227/179.1 |
| 5,368,215 | A | * | 11/1994 | Green et al. | 227/179.1 |

(Continued)

OTHER PUBLICATIONS www.thefreedictionary.com/severable, retrieved Nov. 28, 2011.*

(Continued)

*Primary Examiner* — David Eastwood
(74) *Attorney, Agent, or Firm* — Edwards Wildman Palmer LLP; Scott D. Wofsy; Christopher J. Capelli

(57) ABSTRACT

A trocar needle includes an elongate body having a distal end portion and a proximal end portion, a penetrating tip formed at the distal end portion of the body, and an attachment portion formed at the proximal end portion for attaching a tether thereto. A grip region can further be provided and can be formed for example, at the proximal end portion of the body to facilitate gripping by a surgical grasping device. Additionally or alternatively, a notch or otherwise reduced cross-sectional area can be provided. Such a feature can be formed, for example, at the distal end portion of the body, arranged proximal from a distal end thereof for enhancing haptic perception by a surgeon when utilizing the needle.

19 Claims, 16 Drawing Sheets

(56) References Cited

U.S. PATENT DOCUMENTS

| | | | |
|---|---|---|---|
| 5,573,542 A | 11/1996 | Stevens | |
| 5,928,268 A * | 7/1999 | Butwell et al. | 606/222 |
| 6,746,456 B2 * | 6/2004 | Xiao | 606/144 |
| 6,770,084 B1 | 8/2004 | Bain et al. | |
| 2006/0085036 A1 * | 4/2006 | Viola | 606/228 |
| 2007/0257082 A1 * | 11/2007 | Milliman | 227/175.1 |
| 2009/0082785 A1 * | 3/2009 | Milliman et al. | 606/139 |

OTHER PUBLICATIONS

International Search Report from related PCT Application No. PCT/US2009/043283 dated Dec. 22, 2009.

* cited by examiner

LAPAROSCOPIC GASTRIC AND INTESTINAL TROCAR

CROSS-REFERENCE TO RELATED APPLICATIONS

This application claims the benefit of priority to U.S. Patent Application Ser. No. 61/051,971, filed May 9, 2008, which application is incorporated herein by reference in its entirety.

FIELD OF THE INVENTION

The present invention relates to trocar devices for use in surgical procedures. Particularly, the present invention is directed to a surgical trocar adapted for use in bariatric surgical procedures, including laparoscopic vertical banded gastroplasty, laparoscopic Magenstrasse and Mill procedures, laparoscopic Collis-Nissen gastroplasty, laparoscopic gastric wedge resection, and laparoscopic partial colon resection.

DESCRIPTION OF THE RELATED ART

A variety of surgical devices and techniques are known in the art for performing surgical procedures, including bariatric procedures. Of such devices and techniques, many are directed to restrictive devices and surgical techniques that inhibit excess eating, malabsorptive techniques that reduce the amount of digestion that is allowed to take place, and hormonal manipulation techniques. Restrictive procedures include Lap-Band® (a device manufactured by Allergan, Inc.), vertical banded gastroplasty, and adjustable gastric banding, sleeve gastrectomy, and Magenstrasse & Mill, for example. Malabsorptive techniques include biliopancreatic diversion (or "BPD"), and jejuno-ileal bypass, for example. Procedures that have both restrictive and malabsorptive characteristics include gastric bypass surgery including Roux-en-Y gastric bypass, procedures, for example.

Of these, the Magenstrasse and Mill procedure is relatively simple, effective and safe, and avoids many drawbacks associated with other procedures, such as vertical banded gastroplasty, adjustable banding devices and with other gastric bypass procedures.

Although resulting in an effective morphology, it has proven difficult for surgeons to quickly and accurately place staple lines in the stomach. Moreover, at the terminal end of the staple line, excessive stresses at a junction of opposed staple lines can cause relatively large amounts of tension on the connection, and therefore can impede healing of the area.

Accordingly, there remains a need in the art for procedures and devices that allow for quick and accurate stapling of the stomach along the desired path. There also remains a need in the art for procedures and devices that reduce trauma to the patient and reduce the need for surgical revision. The present invention provides solutions for these needs.

SUMMARY OF THE INVENTION

The purpose and advantages of the present invention will be set forth in and apparent from the description that follows. Additional advantages of the invention will be realized and attained by the methods and systems particularly pointed out in the written description and claims hereof, as well as from the appended drawings.

To achieve these and other advantages and in accordance with the purpose of the invention, in one aspect, a trocar needle is provided including an elongate body having a distal end portion and a proximal end portion, a penetrating tip formed at the distal end portion of the body, and an attachment portion formed at the proximal end portion for attaching a tether thereto. A grip region can further be provided and can be formed, for example, at the proximal end portion of the body to facilitate gripping by a surgical grasping device. Additionally or alternatively, a notch or otherwise reduced cross-sectional area can be provided. Such a feature can be formed, for example, at the distal end portion of the body, arranged proximal from a distal end thereof for enhancing visualization, control and/or haptic perception by a surgeon when using the needle to penetrate tissue. This is particularly beneficial due to the sharpness of the instrument. Such an arrangement provides feedback to the surgeon when that portion of the trocar passes through an anatomical structure by causing a sudden reduction in insertion force, indicating that the needle has passed at least partly into that structure.

The elongate body can be substantially circular in cross-section, or alternatively ovoid or another shape, as desired or required. The body portion can be curved at any angle desired, for example between about 45 and 75 degrees. For example, the body can be curved about 60 degrees. The body can have any length necessary, and can be provided in a variety of lengths. In accordance with a preferred embodiment, the body is about 6.5 cm in length from end to end.

The body can be formed of metal, such as a stainless steel alloy or a titanium alloy for example. Alternatively, the body can be formed of a polymeric material, such as a plastic material, such as polymethylmethacrylate. Alternatively still, the body can be formed of a composite material, such as fiber-reinforced polymer (FRP) or a ceramic material.

The penetrating tip can include one, two, three or more angled facets converging at the distal end of the body of the trocar needle. Alternatively, the penetrating tip can simply be conical in shape, and in accordance with one aspect, the preferred shape is a cutting needle type tip. The attachment portion can include a proximal projection and a distally adjacent recessed portion to engage a tether attached thereto. Alternatively or additionally, the attachment portion can include an eye formed through the body for threading a tether therethrough. The attachment portion can be permanently attached to a tether, the tether being severable from the attachment portion, as in an atraumatic suture needle, for example. In accordance with one aspect of the invention, the attachment portion can be about 0.75 cm in length. The tether can be, for example, elastic surgical tubing. The tether can be formed of a suture material.

The grip region can be recessed on the surface of the body, to facilitate a secure grip with a surgical grasper, and can be formed at the proximal end portion of the body distal to the attachment portion. The grip region, in accordance with the invention, can be tapered downward, approaching the proximal end (opposite the penetrating tip). The grip region can be any suitable dimension. In accordance with one aspect of the invention, the grip is about 0.75 cm in length.

In accordance with another aspect of the invention, a trocar needle assembly is provided including a trocar needle, an anvil for use in conjunction with an circular anastomotic surgical stapler, and a tether connecting the trocar needle to the anvil. The trocar needle can include an elongate body having a distal end portion and a proximal end portion, a penetrating tip formed at the distal end portion of the body, and an attachment portion formed at the proximal end portion for attaching a tether thereto. Additionally, if so desired, a recessed grip region formed at the proximal end portion of the body can be provided, distal to the attachment portion to facilitate gripping by a surgical grasping device. If desired, a notch can be formed at the distal end portion of the body, arranged proximal from a distal end thereof for enhancing haptic perception by a surgeon when utilizing the needle. This notch can be any length desired, but is preferably about 0.75 cm in length and tapers upward from the distal end toward the proximal end of the trocar needle.

The tether can be formed of surgical tubing, such as catheter material or other surgical tubing. Such catheter can be formed of red rubber, for example. Alternatively, the tether can be formed of a suture material. The trocar body can have any suitable diameter. In accordance with one aspect of the invention, the diameter is between about such as about 10 and 20 french (3.3 mm and 6.7 mm). In a preferred embodiment, the diameter is about 12 french (about 4.0 mm). In accordance with another preferred embodiment, the diameter is about 19 french (6.3 mm). The anvil can be sized as needed, but in a preferred embodiment is configured and adapted for use with a 21 mm circular end-to-end anastomosis stapler, such as an Autosuture™ EEA™ stapler manufactured by the United States Surgical division of Tyco Healthcare Group LP. An end-to-end anastomosis surgical stapler having a suitable anvil, which may be used in connection with the present invention is set forth in U.S. Pat. Nos. 5,158,222, 5,285,944, and 6,053,390 to Green et al., which patents are incorporated herein by reference in their entirety.

In accordance with another aspect of the invention, a method of performing a laparoscopic bariatric surgical procedure is provided that provides for precise placement of an EEA anvil. In accordance with the invention, a method of performing a Magenstrasse and Mill bariatric surgical procedure is provided, which includes the steps of gaining access to a peritoneal cavity of the patient, insufflating the peritoneal cavity, creating an access path to the stomach, passing a gastric trocar having an end-to-end anastomosis anvil tethered thereto through the posterior and anterior walls of the stomach, pulling the end-to-end anastomosis anvil through an opening formed by the gastric trocar, detaching the end-to-end anastomosis anvil from the trocar, mating the end-to-end anastomosis anvil with an end-to-end anastomosis stapler, actuating the end-to-end anastomosis stapler to form a circular aperture through the stomach and mutually attaching the anterior and posterior walls to one another at the aperture. The method can further include inserting a linear surgical stapler partially into the aperture, transecting the stomach substantially linearly from the aperture toward the Angle of His with the linear surgical stapler, oversewing the circular portion of the staple line formed in the stomach with manual suture.

The step of passing the gastric trocar having an end-to-end anastomosis anvil tethered thereto through the posterior and anterior walls of the stomach can occur at any necessary location, and in a preferred embodiment between about 5 mm and 6 mm from the pylorus.

The step of passing a gastric trocar having an end-to-end anastomosis anvil tethered thereto through the posterior and anterior walls of the stomach can occur from the posterior side to the anterior side. Alternatively, this step can occur from the anterior side to the posterior side.

The step of oversewing the circular portion of the staple line can be performed with a suture formed of an absorbable material, such as one formed of polyglycolic acid. Also, the step of oversewing the circular portion of the staple line can be performed with a running stitch.

The step of detaching the end-to-end anastomosis anvil from the trocar can be performed by severing the tether.

The step of inserting a linear surgical stapler partially into the aperture can include placing a first stapling portion of the linear surgical stapler adjacent the external surface of the posterior stomach wall and placing a cooperating stapling portion adjacent the external surface of the anterior stomach wall. The surgical stapler is preferably sized appropriately and can be, for example, a stapler having a width of about 45 mm or 60 mm, and can have 6 rows of staples, such as a 6 row blue Autosuture™ Endo-GIA™ stapler manufactured by the United States Surgical division of Tyco Healthcare Group LP. Such as stapler is described in U.S. Pat. Nos. 5,540,375 and 5,690,269 to Bolanos et al., which patents are incorporated herein by reference in their entirety.

The step of actuating the end-to-end anastomosis stapler can form a substantially circular aperture.

The step of transecting the stomach substantially linearly can be performed based on the lesser curvature of the stomach.

The step of transecting the stomach can be performed using 45 mm stapler one, two or more times and then a 60 mm stapler one or more times.

A gastric pouch can be created based on the lesser curvature. This pouch can be completely transected from the stomach at the Angle of His.

Following the step of transecting the stomach, the stapled regions can be inspected for excessive bleeding. If an area is found to bleeding, the area can be suture ligated or clipped.

Following the step of oversewing the circular portion of the staple line, the stapled regions can again be inspected for excessive bleeding.

The step of closing surgical access paths can include closing a facial defect created by an access port used for insertion of a surgical stapler. The step of closing surgical access path can be at least partly accomplished using an interrupted stitch using a laparoscopic transfascial suture passer. A polydioxanone suture material can be used for this purpose, for example.

The step of creating an access path to the stomach can include the steps of dissecting a fat pad at a gastroesophageal junction, with an ultrasonic scalpel, for example, dividing the gastrocolic omentum below the gastro-epiploic vessels to enter the lesser sac, and dissecting posterior avascular adhesions between the pancreas and stomach.

The step of gaining access to the peritoneal cavity can include the steps of inserting a 5 mm port for a liver retractor, and inserting three 10-12 mm ports across the upper abdomen as the main operating ports. The liver retractor can be a Nathanson-type liver retractor, which can be inserted in the subxiphoid region.

It is to be understood that is conceived that any feature described in connection with any particular embodiment in accordance with the invention can be advantageously applied to other embodiments in accordance with the invention, even if not explicitly set forth herein.

It is also to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the method and system of the invention. Together with the description, the drawings serve to explain the principles of the invention, wherein.

DETAILED DESCRIPTION

Reference will now be made in detail to the present preferred embodiments of the invention, examples of which are illustrated in the accompanying drawings. The methods and corresponding steps of the invention will be described in conjunction with the detailed description of the devices. The devices and methods presented herein may be used in surgical procedures. The present invention is particularly suited for use in bariatric surgical procedures.

Figure 1:
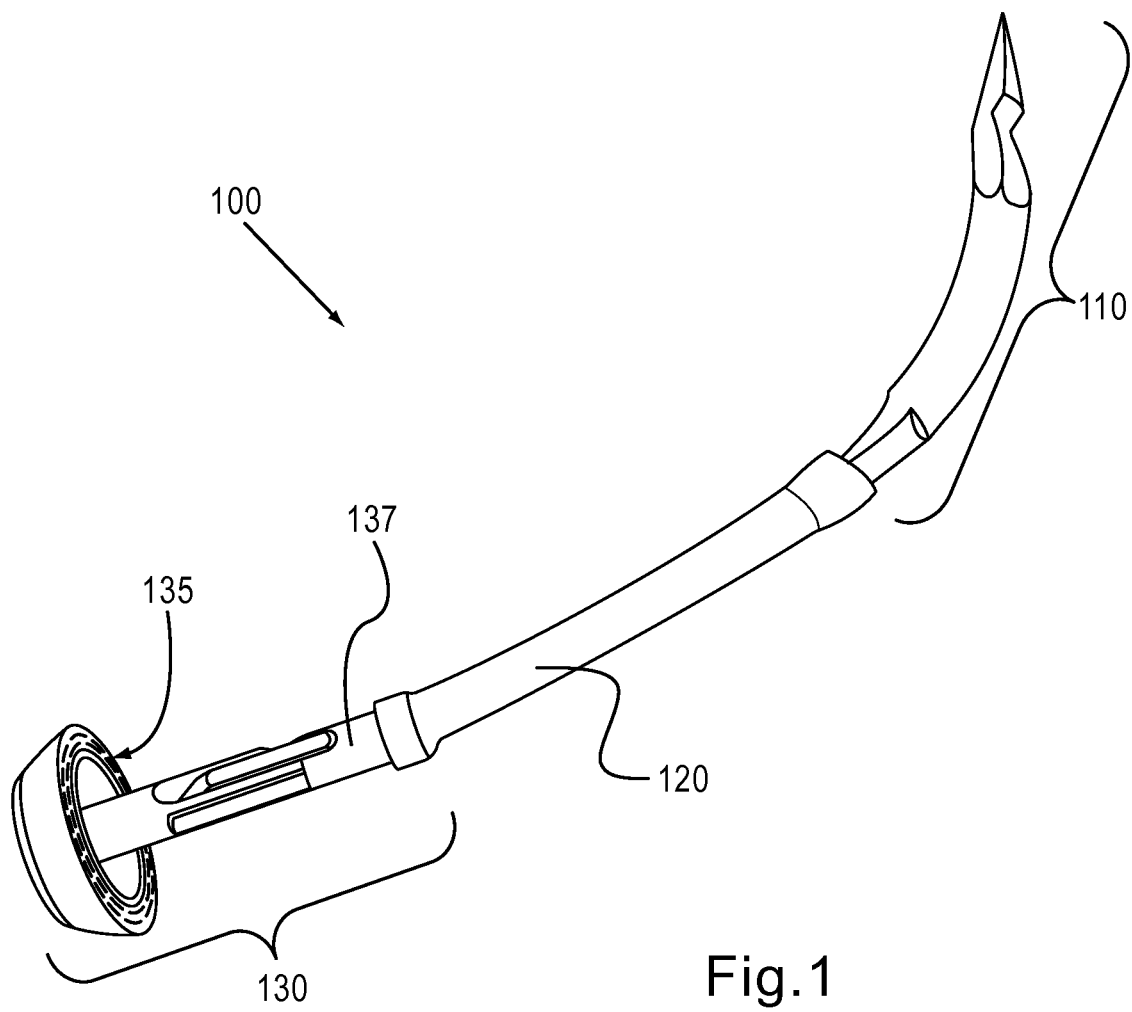
FIG. 1 is an isometric view of a gastric trocar assembly including a gastric trocar needle in accordance with the invention.
Figure 2:
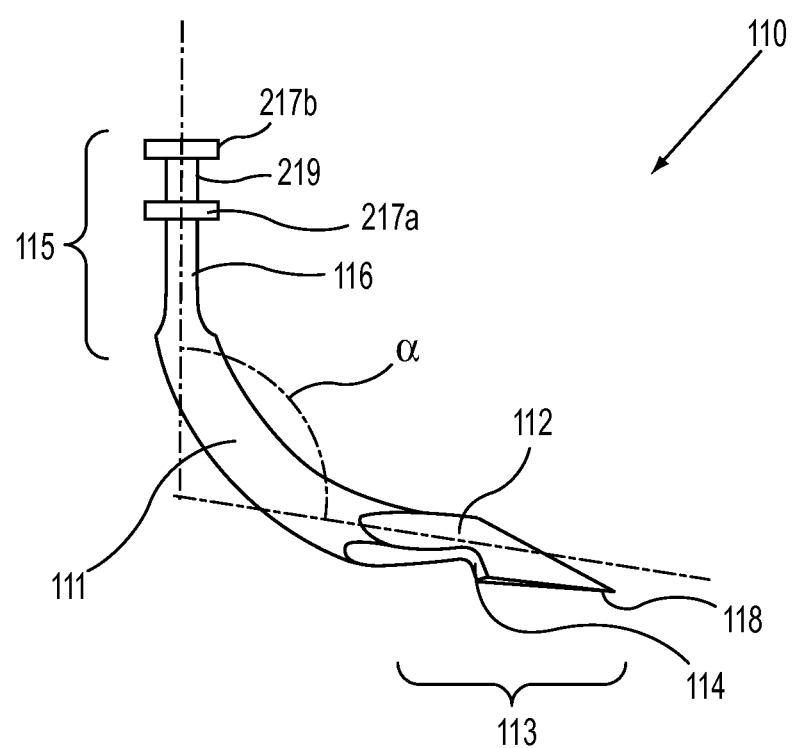
FIG. 2 is a side view of a gastric trocar needle in accordance with the invention.
Figure 3:
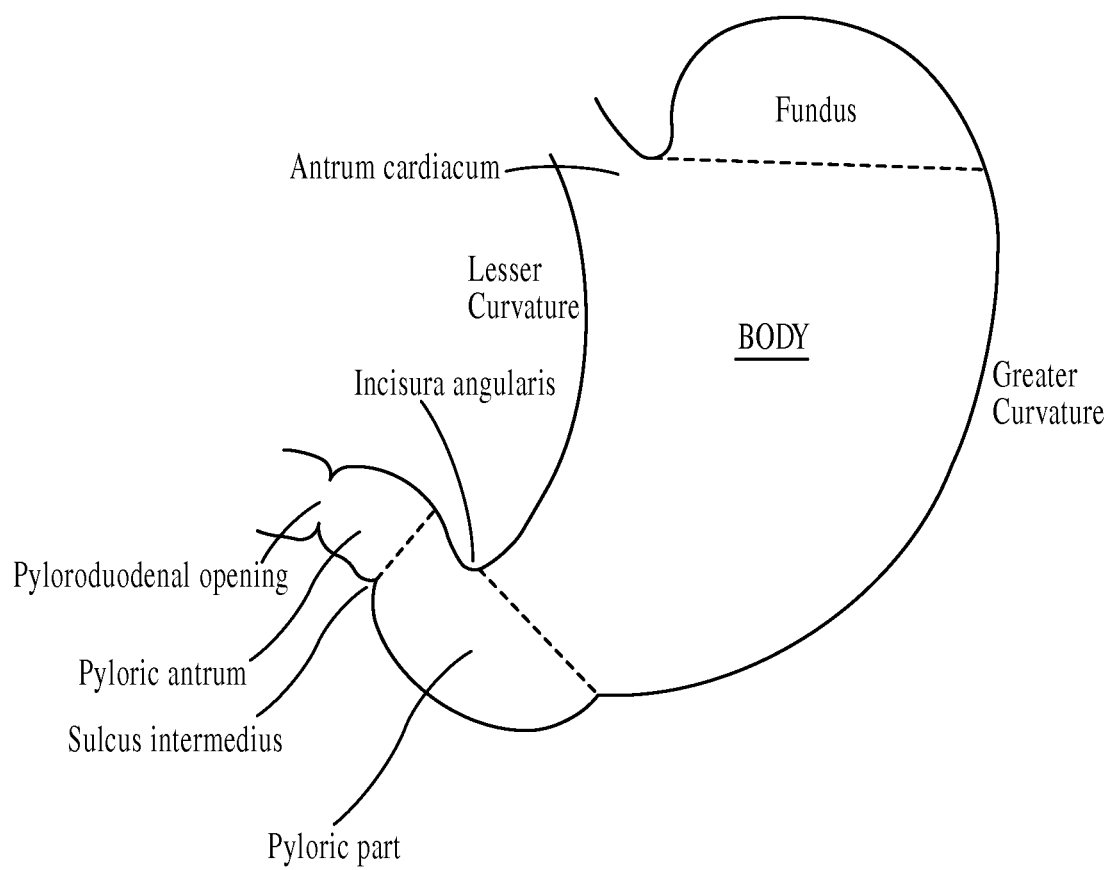
FIG. 3 illustrates various regions of the stomach.
Figure 4:
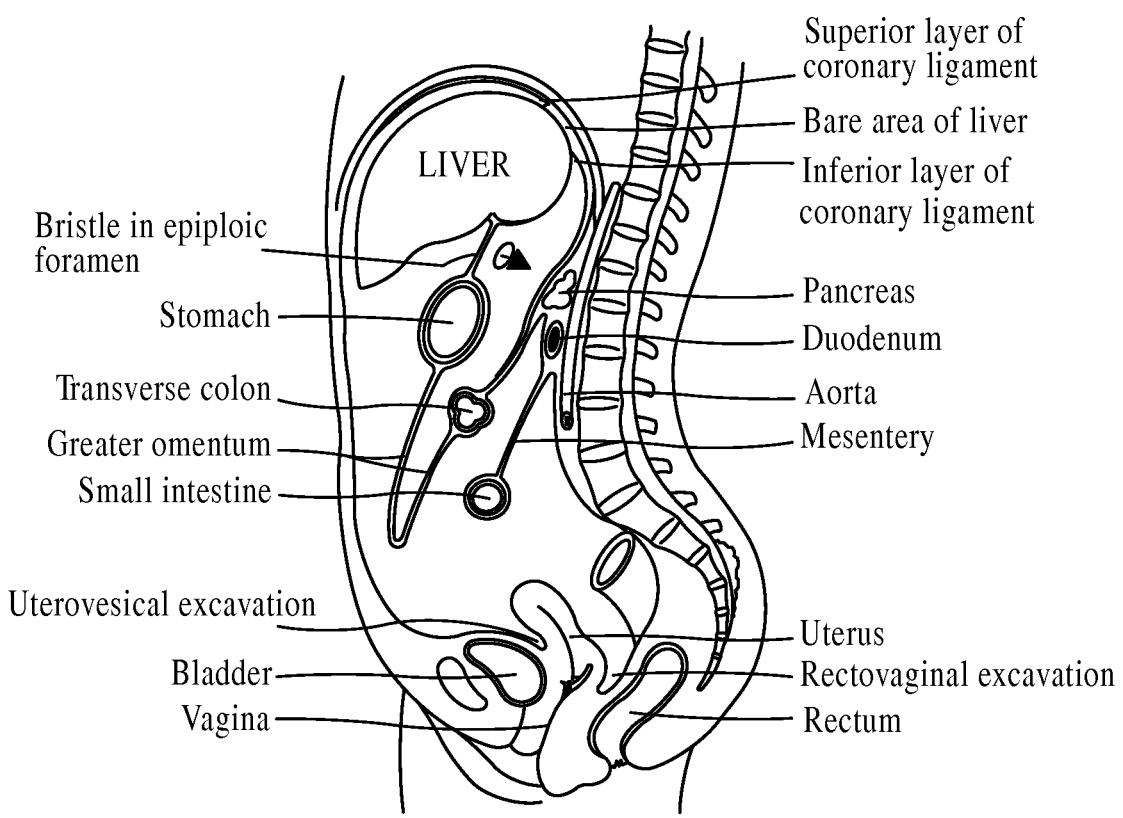
FIG. 4 is a cross-sectional illustration of a human abdominal cavity showing orientation of various anatomical structures.

In accordance with the invention, as illustrated in FIGS. 1 and 2, for example, a trocar needle assembly 100 is provided, which includes a trocar needle 110, an anvil 130 for use in conjunction with an circular anastomotic surgical stapler, and a tether 120 connecting the trocar needle 110 to the anvil 130. As illustrated in FIG. 2, for example, the trocar needle 110 can include an elongate body 111 having a distal end portion 113 and a proximal end portion 115. As illustrated, a penetrating tip 118 can be formed at the distal end portion 113 of the body 111, and one or more attachment portions 217a,b can be formed at the proximal end portion 115 for attaching a tether 120 (FIG. 1) thereto. Additionally, if so desired, a recessed grip region 116 formed at the proximal end portion 115 of the body 111 can be provided, distal to the attachment portions 217a,b to facilitate gripping by a surgical grasping device. If desired, a notch 114 can be formed at the distal end portion 113 of the body 111, arranged proximal from the penetrating tip 118. The notch 114 can aid in enhancing haptic perception by a surgeon when utilizing the needle 110. Such an arrangement can provide feedback to the surgeon when that portion 114 of the trocar body 111 passes through an anatomical structure by causing a sudden reduction in insertion pressure or force.

The tether 120 (FIG. 1) can be formed of any suitable material, such as surgical tubing, which may be a catheter material or another type. Such catheter can be formed of a red rubber or silicone, for example. Alternatively, the tether can be formed of a suture material, and attached to the needle 110 by way of an eye or other attachment element formed on the needle 110.

The trocar body 111 can have any suitable diameter. In accordance with a preferred embodiment, the body 111 has a diameter of about 19 french (about 6.3 mm).

The anvil 130 can be sized as needed, and includes a stapling region 135 and a shaft 137 for engaging an anastomotic stapler, as well as the tether 120. In a preferred embodiment, the anvil 130 is configured and adapted for use with a 21 mm circular end-to-end anastomosis stapler, such as an Autosuture™ EEA™ stapler manufactured by the United States Surgical division of Tyco Healthcare Group LP. As set forth hereinabove, U.S. Pat. Nos. 5,158,222, 5,285,944, and 6,053,390 to Green et al. describe circular stapling suitable for use in connection with the present invention.

With particular reference to FIG. 2, which shows an isolated view of the trocar needle 110, the elongate body 111 can be substantially circular in cross-section, or alternatively ovoid or another shape, as desired or required. The body portion 111 can be curved at any angle α (alpha) (FIG. 2) desired, for example between about 45 and 75 degrees. In a preferred embodiment, the body 111 can be curved by an angle α (alpha) of about 60 degrees.

The body 111 or any portion thereof can be formed of metal, such as a stainless steel alloy or titanium alloy for example. Alternatively, the body 111 can be formed of a polymeric material, such as a plastic material, such as polymethylmethacrylate. Alternatively still, the body 111 or any portion thereof can be formed of a composite material, such as fiber-reinforced polymer (FRP) or a ceramic material. If so desired, different parts of the body 111 can be formed of different materials and joined together to form the whole body 111.

The distal end portion 113 can include one, two, three or more angled facets 112 converging at the penetrating tip 118 of the body 111 of the trocar needle 110.

The proximally arranged attachment portion or portions 217a, 217b can include one or more projections and may also include a distally recessed portion 219 to facilitate engagement of a tether thereto. Alternatively or additionally, the attachment portion 217a,b can include one or more eyes formed through the body 111 for threading a tether therethrough. Moreover, a tether can be either removably or permanently attached to the attachment portion or portions 217a, b. In either case, the tether can be removed by severing the tether. In the case of a separable tether, severing of the tether is optional. The tether can be any suitable material, but in a preferred embodiment is elastic surgical tubing, into which the attachment portion(s) 217a,b is (are) inserted. The elasticity of the tubing, in this instance, engages the attachment portion(s) 217a,b. Alternatively, the tether can be formed of a suture material that is passed through an eye formed in the trocar body 111. Naturally, as can be seen from FIG. 1, the end of the tether 120 not connected to the trocar needle 110 is attached to an anvil 130. The shaft 137 of the anvil 130 is also inserted into the tubular tether 120. If chosen appropriately, the materials used for the tether 120 can be such that the elasticity thereof and frictional forces between the tether 120 and the anvil shaft 137 maintain a secure connection therebetween.

The grip region 116 of the needle body 111 can be recessed from the surface of the body 111, to facilitate a secure grip by an instrument, such as a surgical grasper, for example. Although a grip region 116 can be provided in any location on the body 111, in the illustrated embodiment, the grip region 116 is formed at the proximal end portion of the body distal to the attachment portion(s) 217a,b.

If so desired, one or more kits, having one or more sizes of the various components of the gastric trocar assembly 100 can be provided. For example, a kit can be provided for use in an operating room, having a wide range of sizes, particularly diameters, of anvils 130, a range of sizes, including length an/or diameter of the trocar needle 110, and assorted lengths of tether material, allowing the surgeon to determine what combination of sizes of elements would be most appropriate for any particular patient. Similarly, due to the relatively specialized nature of Circular surgical staplers, kits in accordance with the invention can simply include a range of needle 110 sizes, and optionally a range of tether sizes. In such an instance, the anvil 130 can be selected from a different kit, provided separately.

Figure 5A:
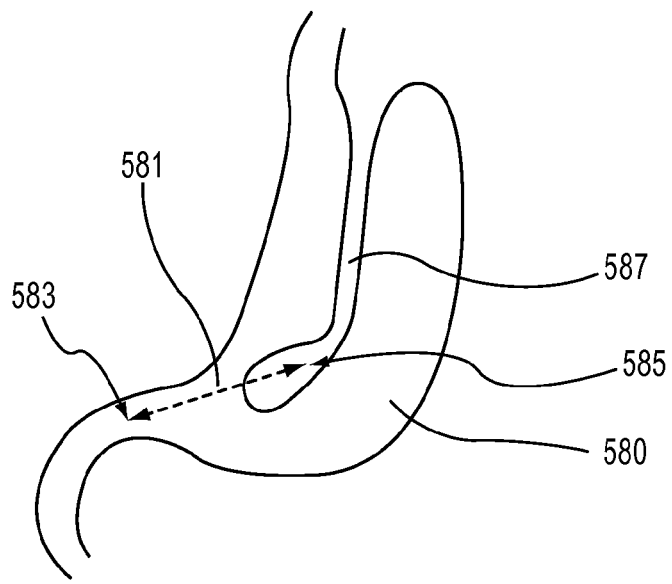
FIG. 5A schematically illustrates an example stomach following a Magenstrasse and Mill procedure.
Figure 5B:
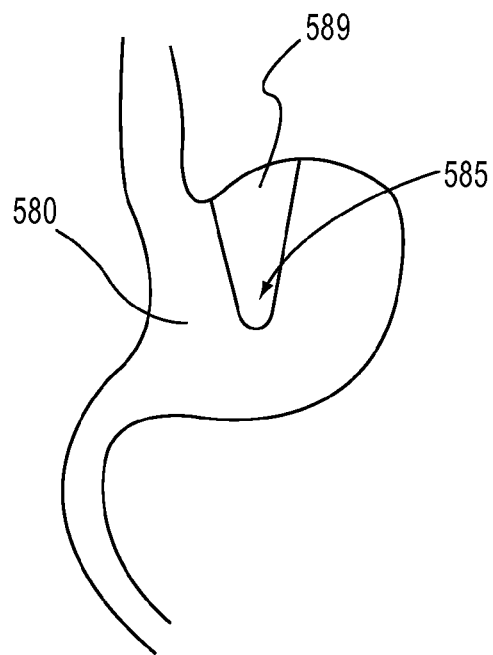
FIG. 5B illustrates where tissue removal occurs when performing a gastric wedge resection procedure in accordance with the invention.

In accordance with another aspect of the invention, methods of performing bariatric surgical procedures are provided. With reference to FIGS. 5A and 5B, methods in accordance with the invention include the step of passing the gastric trocar 110 through the stomach wall in a location necessary to commence stomach division or resection, which, depending on the particular procedure can occur at any necessary location. As illustrated in FIG. 5A, in a laparoscopic Magenstrasse and Mill procedure, the pylorus 583 is used as a reference point, with the subject gastric trocar 110 being placed a distance 581 from the pylorus 583. The substantially circular aperture 585 formed by the initial puncture of the stomach 580 is then used as a reference for placing the linear stapler to form a linear separation 587, as will be discussed in more detail below. In a preferred embodiment, the distance 581 is between about 5 mm and 6 mm from the pylorus 583.

FIG. 5B illustrates the manner in which a laparoscopic gastric wedge resection would be performed in accordance with the invention. First, an aperture 585 is formed through the stomach 580, after which the stomach is resected along two opposed lines, forming a wedge 589 therebetween. As with a laparoscopic Magenstrasse and Mill procedure, this step can be performed using linear surgical staplers.

Figure 6:
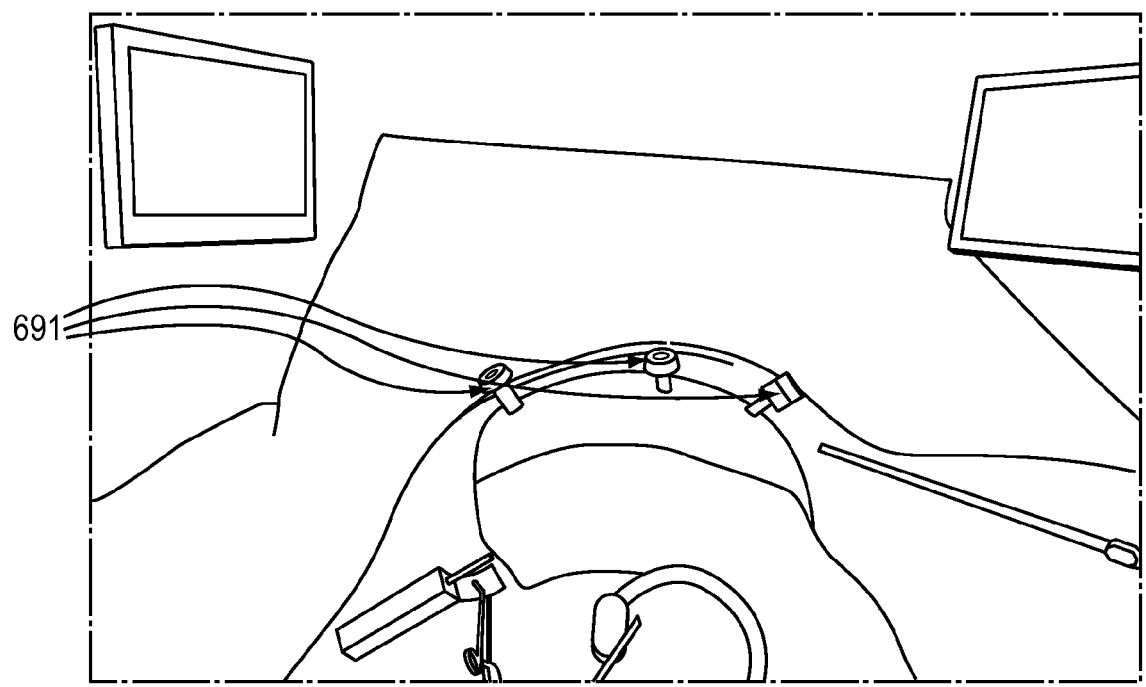
FIGS. 6-25 illustrate example steps of performing a Magenstrasse and Mill bariatric surgical procedure in accordance with the invention.

In accordance with one of these aspects, and as illustrated in FIGS. 5A and 6-25, a method of performing a Magenstrasse and Mill bariatric surgical procedure is provided. The method includes the step of gaining access to a peritoneal cavity of the patient, which as illustrated in FIG. 6 can be achieved through one or more surgical access ports 691. Typically, such ports 691 are inserted following insufflation of the peritoneal cavity, such as with a veress needle, for example.

The step of gaining access to the peritoneal cavity can include the steps of inserting a 5 mm port for a liver retractor, and inserting three 10-12 mm ports across the upper abdomen. The liver retractor can be a Nathanson-type liver retractor, and the 5 mm port can be inserted below the xipohid process.

The method further includes creating an access path to the stomach 580, as necessary, depending on the precise point of entry. In accordance with one aspect, this step includes the steps of dissecting a fat pad at a gastroesophageal junction, which can be accomplished with an ultrasonic scalpel, for example, dividing a gastrocolic omentum below the gastroepiploic vessels to enter the lesser sac, and dissecting posterior adhesions in the lesser sac between the pancreas and stomach.

Figure 7:
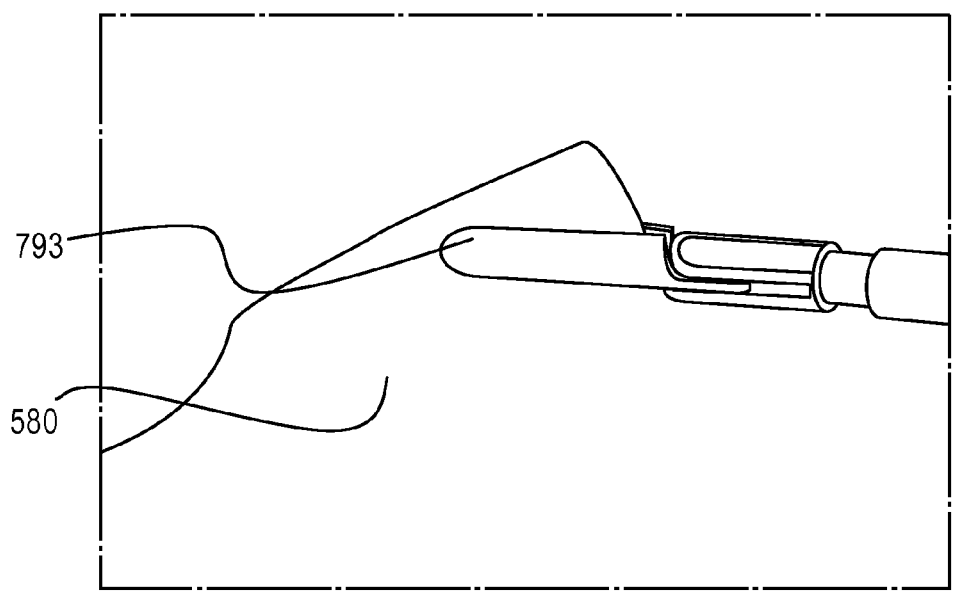
Figure 8:
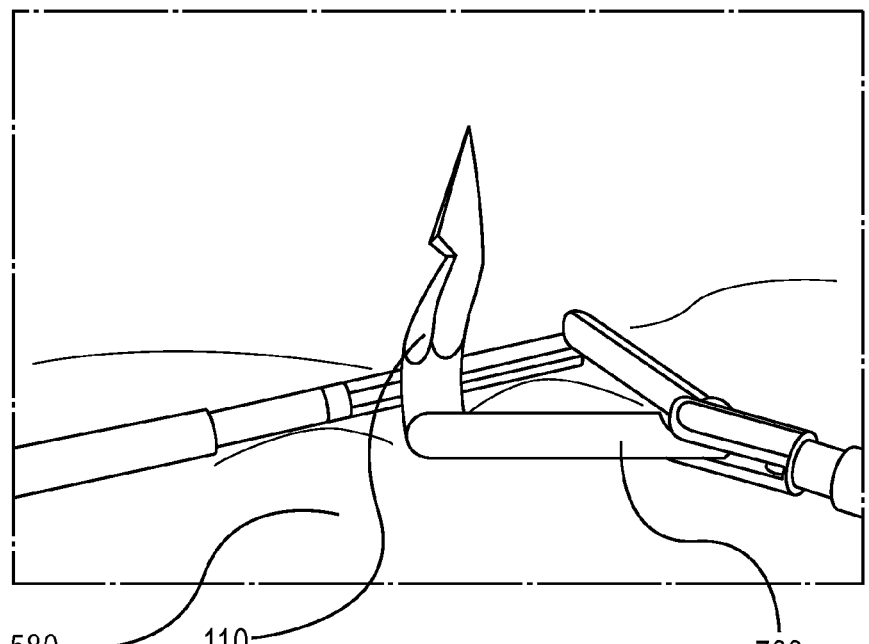

As shown in FIGS. 7 and 8, when the stomach 580 is accessible on both dorsal and ventral sides, a gastric trocar needle 110 having an end-to-end anastomosis anvil 130 tethered thereto is passed into the lesser sac and punctures the posterior and anterior walls of the stomach 580. A surgical grasper 793 can be used to facilitate puncture of the stomach 580. This action pulls the end-to-end anastomosis anvil 130 through an opening formed by the gastric trocar needle 110.

Figure 9:
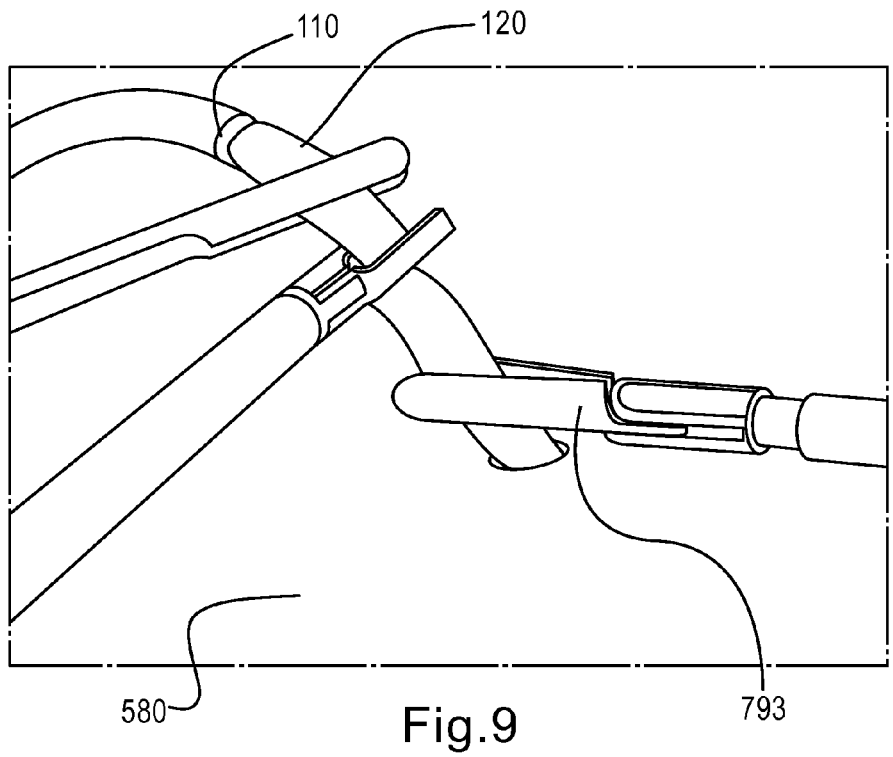
Figure 10:
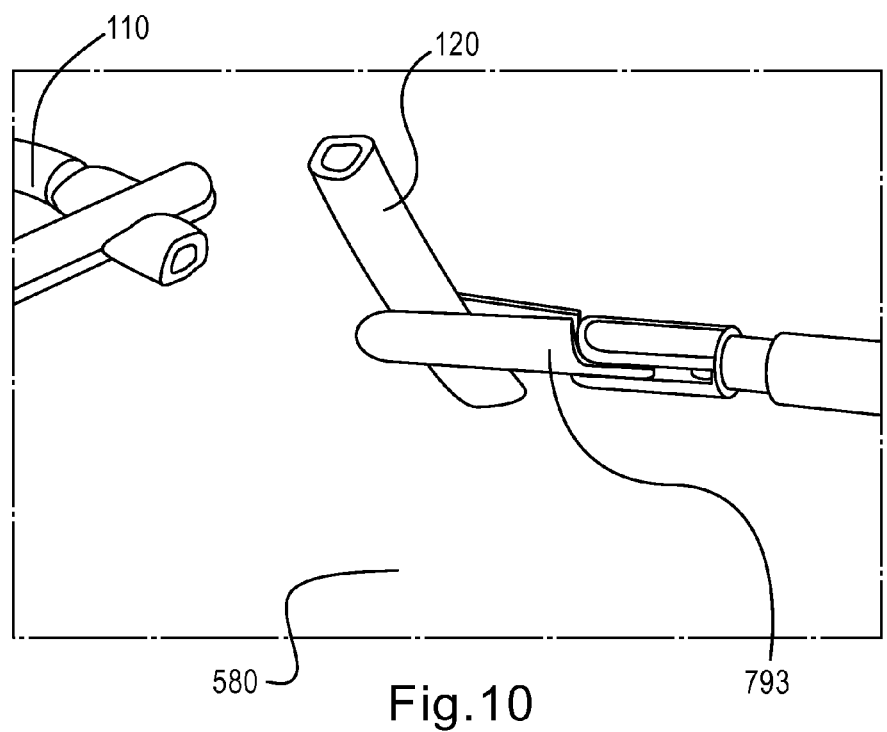

As shown in FIGS. 9-10, the trocar needle 110 can be removed from the tether 120 once the tether 120 is sufficiently through the aperture. This point for removal of the trocar needle 110 is advantageous to limit risk of damage due to the sharp trocar needle 110. Alternatively, the needle 110 can remain connected to the tether 120.

Figure 11:
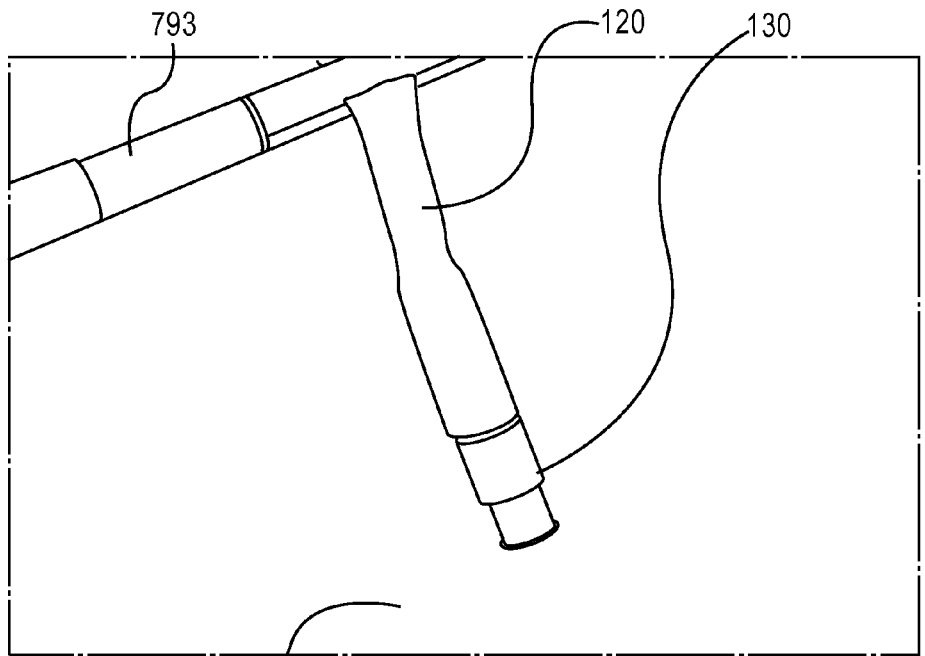
Figure 12:
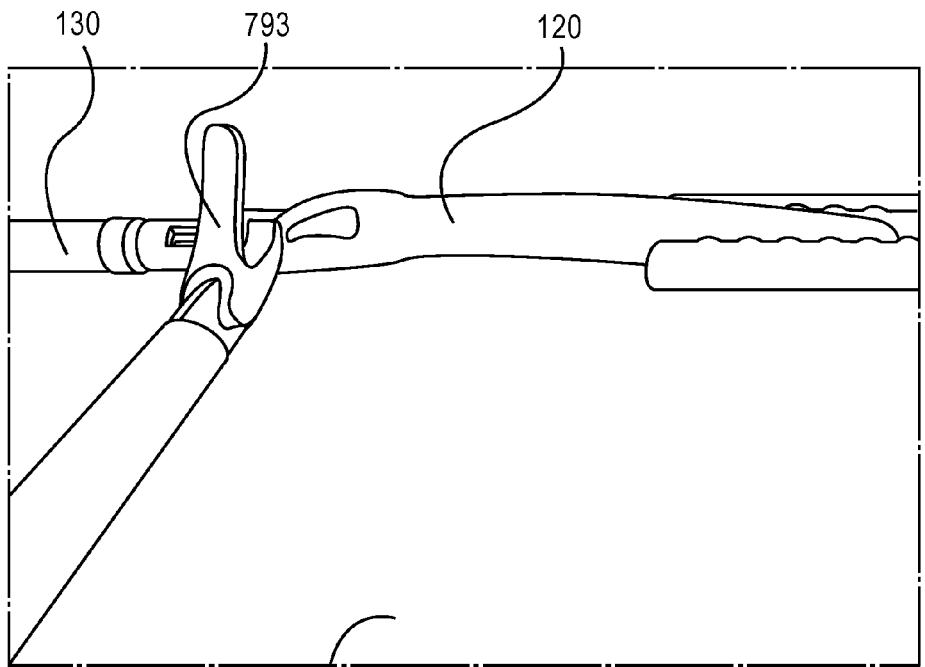
Figure 13:
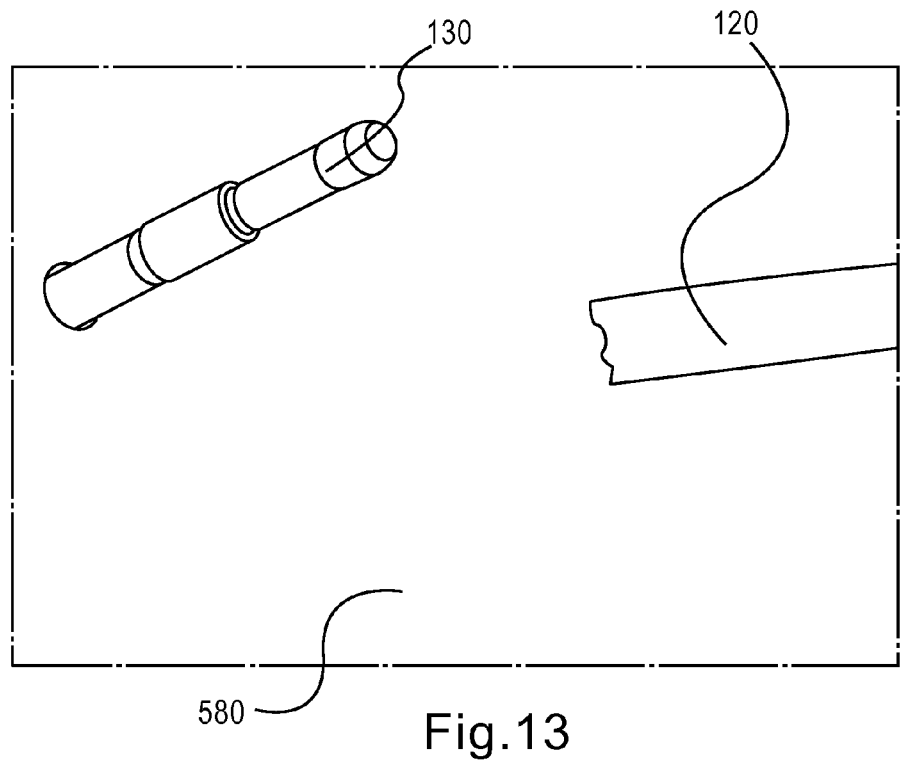

As shown in FIG. 11, the anvil 130 is pulled until it meets resistance with the walls of the stomach 580. Next, the end-to-end anastomosis anvil 130 is detached from the trocar needle 110. Although as illustrated in FIG. 1, the anvil 130 can simply be pulled from the tether 120, this step is preferably performed by severing the tether 120, as illustrated in FIG. 12. Specifically, as illustrated, the tether 120 is split longitudinally to release the anvil 130 with a surgical instrument 793. Any surgical instrument suitable for the purpose can be used to sever the tether 120, such as a scalpel, electrocautery device, or an ultrasonic coagulating instrument, such as an ultrasonic scalpel. Due to the limited access afforded by laparoscopic surgical techniques, it is difficult to apply force sufficient to pull the anvil 130 from the tether without also severing the tether 120. Alternate arrangements, such as a rip cord in the tether 120, to release the anvil 130 when actuated, can be provided as alternatives. FIG. 13 illustrates the anvil 130 removed from the tether 120.

Figure 14:
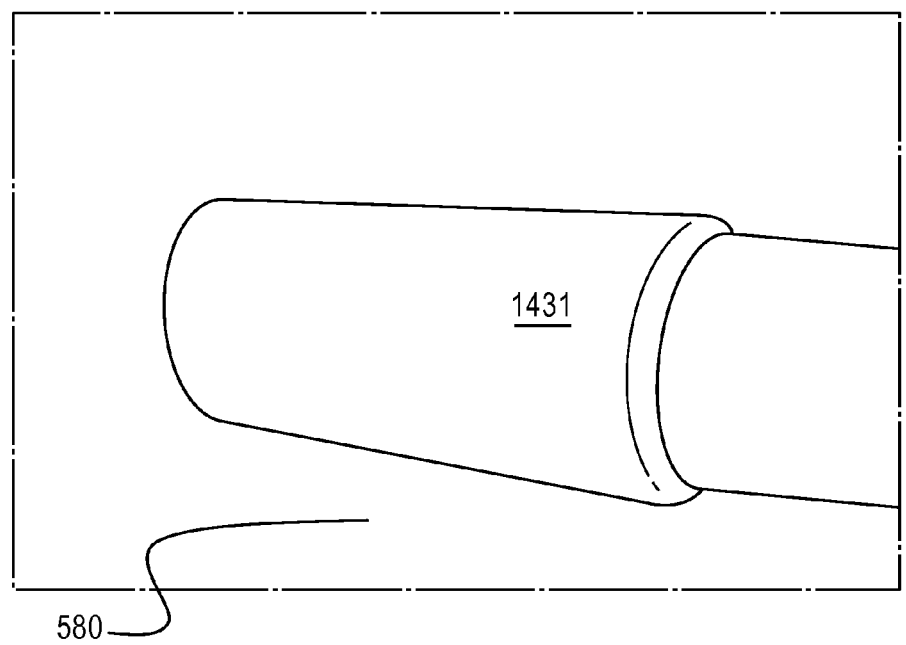
Figure 15:
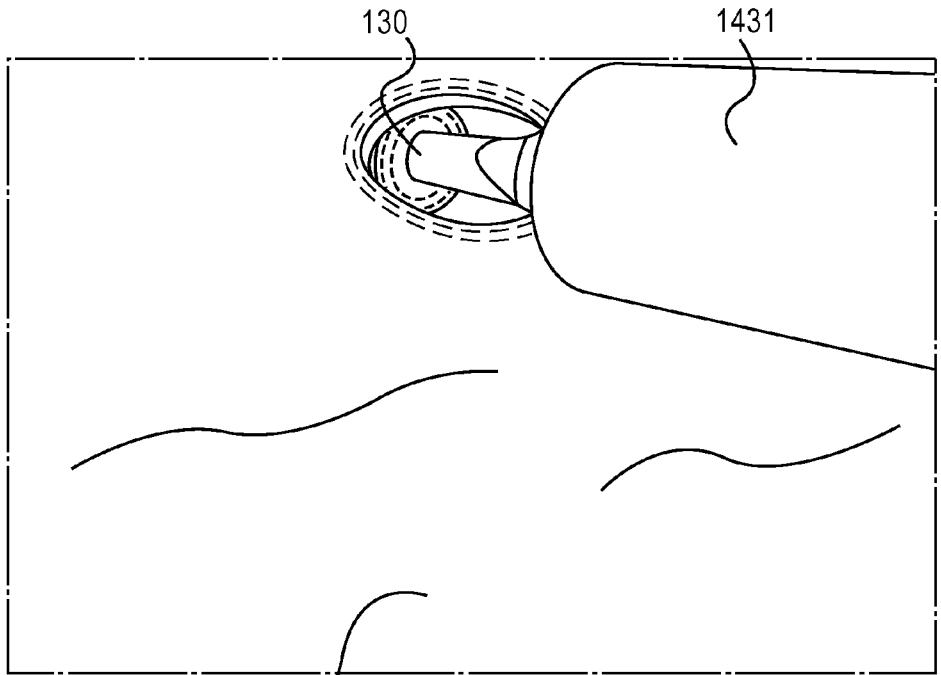
Figure 16:
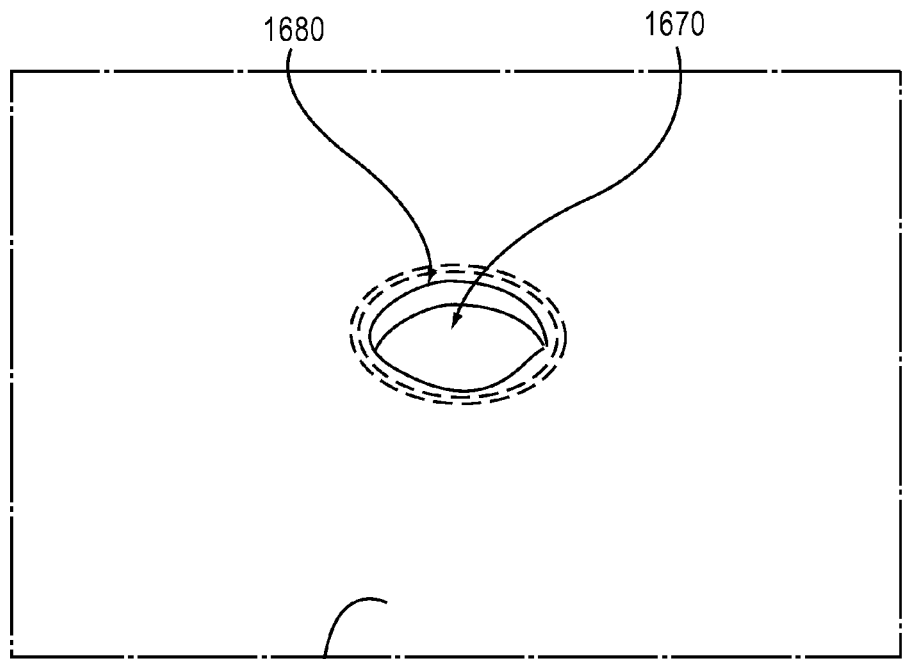
Figure 17:
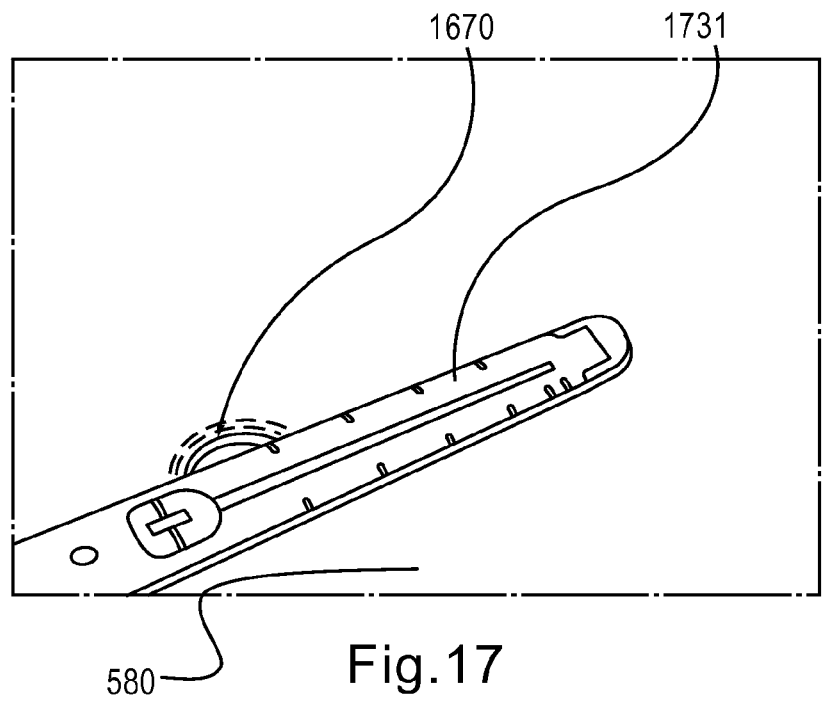
Figure 18:
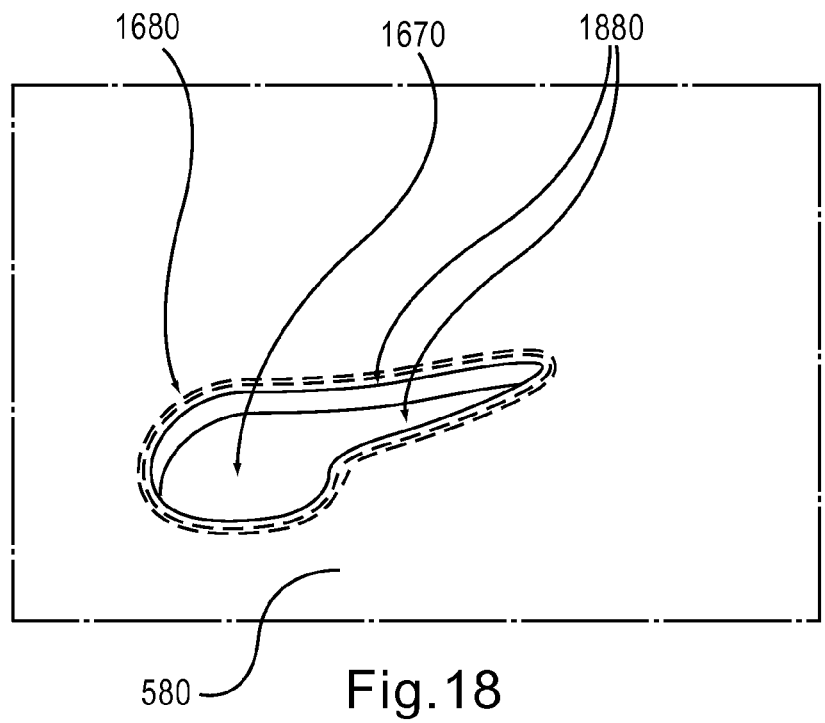
Figure 19:
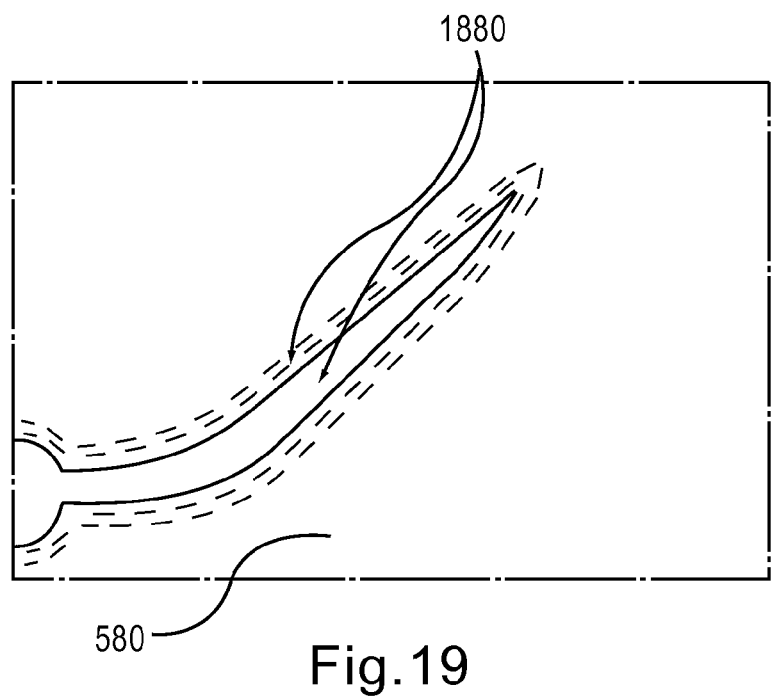
Figure 20:
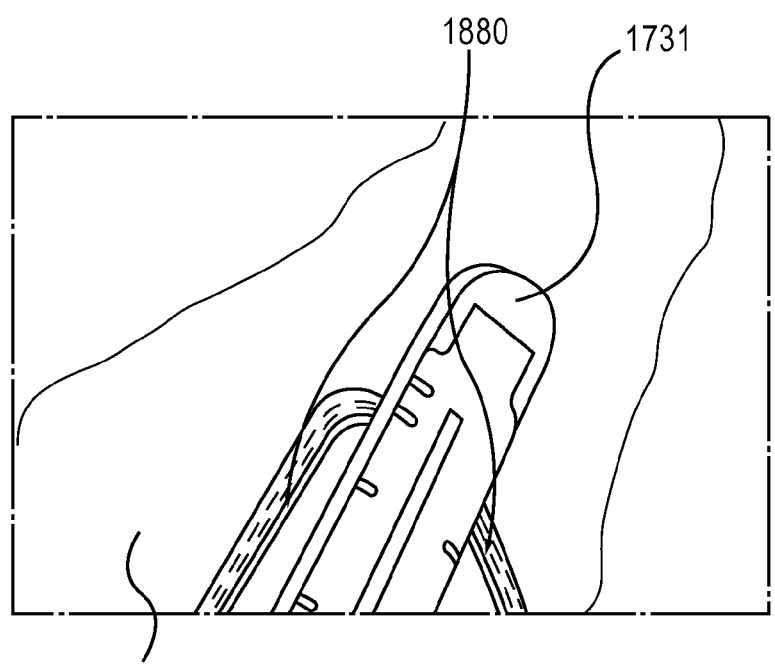
Figure 21:
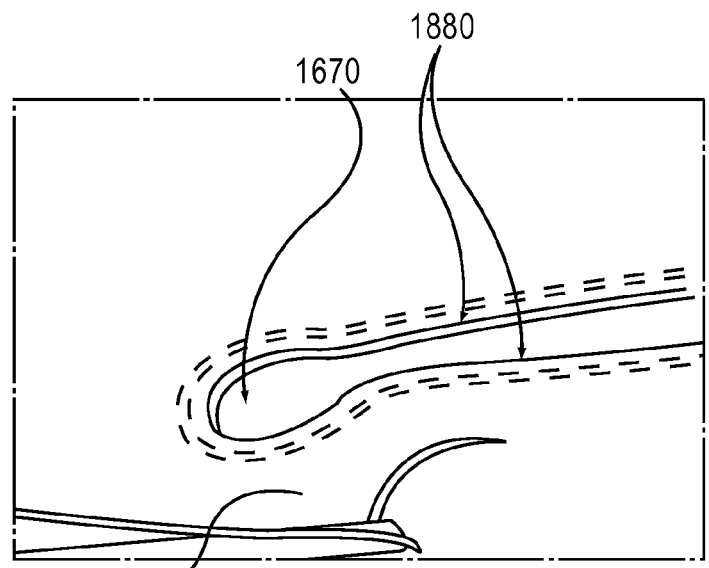

Subsequently, as illustrated in FIGS. 14-16, the anvil 130 is mated with a compatible end-to-end anastomosis stapler 1431. Actuating the end-to-end anastomosis stapler then inserts a circular array of staples 1680 around, while simultaneously forming an aperture 1670 through the stomach 580. The staples 1680 mutually attach the anterior and posterior walls of the stomach 580 to one another.

As illustrated in FIGS. 17-21, a linear surgical stapler 1731 can then be partially inserted into the aperture 1670, inserting staple lines 1880 and transecting the stomach 580 substantially linearly from the aperture 1670 toward the Angle of His with the linear surgical stapler 1731. In creating a gastric pouch, the pouch size is determined by placing various size bougies in the stomach and pressing it against the lesser curvature of the stomach.

The linear surgical stapler can be inserted partially into the aperture 1670 can include placing a first stapling portion of the linear surgical stapler 1731 adjacent the external surface of the posterior stomach wall and placing a cooperating stapling portion adjacent the external surface of the anterior stomach wall. The surgical stapler 1731 is preferably sized appropriately. In accordance with one aspect of the invention, the stapler 1731 has a width of about 45 mm or 60 mm, and has 6 rows of staples. One stapler meeting these criteria is a 6 row blue Autosuture™ Endo-GIA™ stapler manufactured by the United States Surgical division of Tyco Healthcare Group LP, for example.

In accordance with the invention, the step of transecting the stomach 580 substantially linearly can be performed based on the lesser curvature of the stomach 580. Moreover, in accordance with one aspect, this step can be performed using 45 mm stapler one, two or more times and then a 60 mm stapler one or more times. The gastric pouch is completely transected from the Angle of His down to the level of the previously created circular staple line formed by the EEA stapler. Further, following the step of transecting the stomach, the stapled regions can be inspected for excessive bleeding. If an area is found to bleeding, the area can be suture ligated or clipped.

Figure 22:
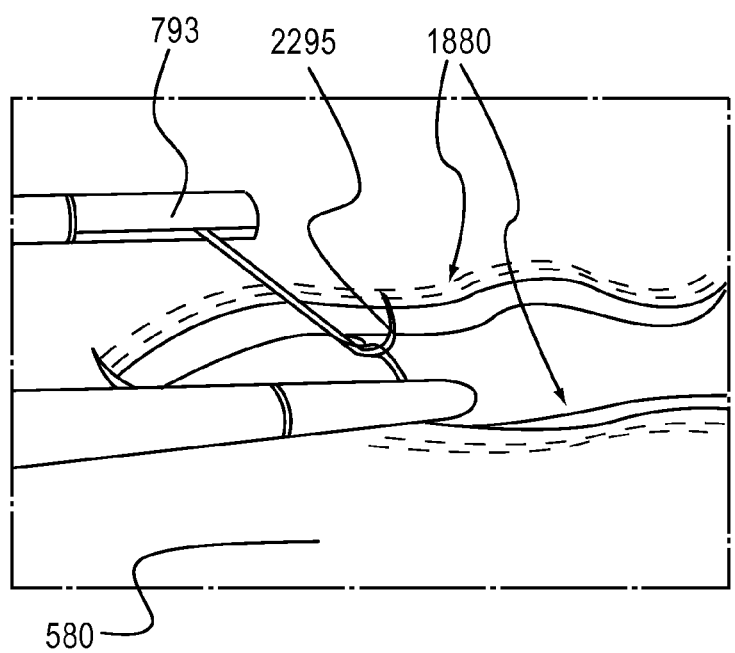
Figure 23:
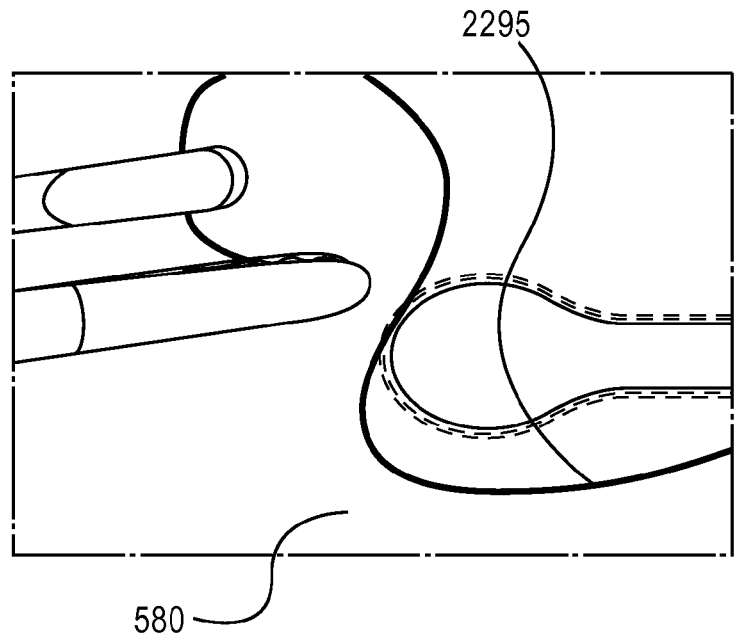
Figure 24:
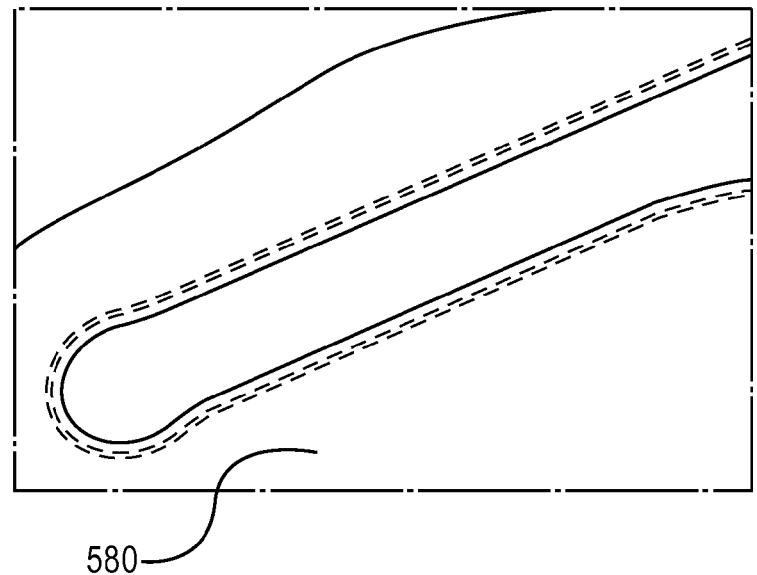

As shown in FIGS. 22-23, the circular portion of the staple line 1680 surrounding the aperture 1670 can then be oversewn manually with a suture material 2295 to reinforce the region. A suture 2295 formed of an absorbable material, such as one formed of polyglycolic acid can be used. Any suitable stitch can be used for this purpose, such as a running stitch. Following the step of oversewing the circular portion of the staple line, the stapled regions can again be inspected for excessive bleeding.

Figure 25:
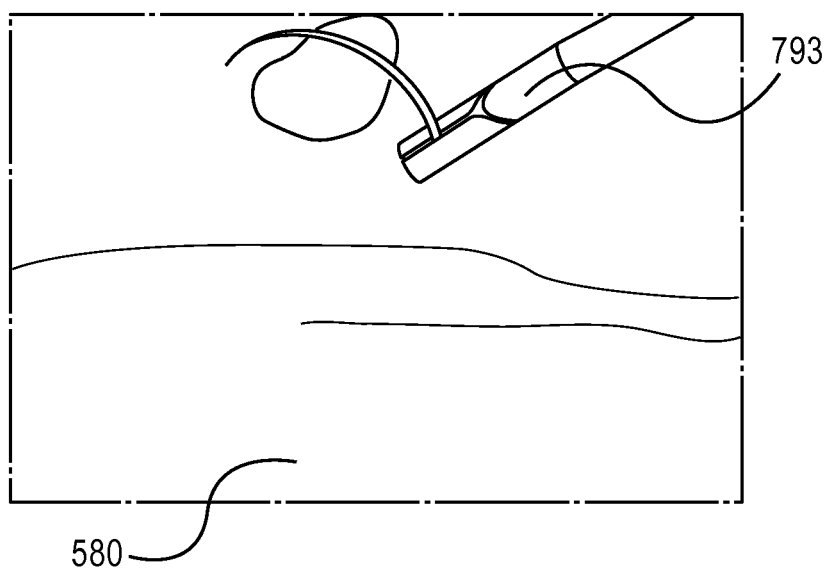

As shown in FIG. 25, the step of closing surgical access paths can include closing a facial defect created by an access port 691 used for insertion of a surgical stapler 1731. The step of closing surgical access path can be at least partly accomplished using an interrupted stitch. An absorbable material, such as a polydioxanone suture material can be used for this purpose, for example.

In accordance with the invention, various aspects of the subject methods can include the following additional steps or modifications.

As desired or appropriate, the step of passing a gastric trocar 100 through the posterior and anterior walls of the stomach can occur from the posterior side to the anterior side. Alternatively, this step can occur from the anterior side to the posterior side.

The methods and systems of the present invention, as described above and shown in the drawings, provide for devices and methods that facilitate relatively fast and safe bariatric surgical procedures, such as a Magenstrasse and Mill procedure. It will be apparent to those skilled in the art that various modifications and variations can be made in the device and method of the present invention without departing from the spirit or scope of the invention. Thus, it is intended that the present invention include modifications and variations that are within the scope of the appended claims and their equivalents.

What is claimed is:

1. A trocar needle comprising:
   (a) a curved elongate body having an outer circumference, a distal end portion, a proximal end portion and an outer circumferential surface, said outer circumferential surface transitioning proximally to a recessed grip region at the proximal end portion, said recessed grip region having opposed surfaces recessed from the outer circumferential surface;
   (b) a penetrating tip formed at the distal end portion of the body and at least one angled facet converging at the penetrating tip; and
   (c) a notch formed at the distal end portion of the curved body, immediately proximal the penetrating tip, the notch being defined by a surface extending between the outer circumferential surface and the at least one angled facet thereof, said notch configured for enhancing visualization, control and haptic perception by a surgeon when utilizing the needle.

2. The trocar needle of claim 1, wherein the elongate body is substantially circular in cross-section.

3. The trocar needle of claim 1, wherein the elongate body is curved such that the proximal end portion and the distal end portion of the elongate body are oriented in respective directions which are substantially transverse relative to one another.

4. The trocar needle of claim 3, wherein the elongate body is curved between 45 and 75 degrees.

5. The trocar needle of claim 1, wherein the body is formed of a metal.

6. The trocar needle of claim 5, wherein the body is formed of a stainless steel alloy.

7. The trocar needle of claim 1, including two or more angled facets converging at the penetrating tip.

8. The trocar needle of claim 1, wherein the grip region formed at the proximal end portion of the body is configured to facilitate gripping by a surgical grasping device.

9. The trocar needle of claim 8, wherein the grip region is formed at the proximal end portion of the body distal to an attachment portion.

10. A trocar needle assembly comprising:
    (a) an anvil;
    (b) a tether having first and second opposing ends wherein a first end is coupled to the anvil; and
    (c) a trocar needle coupled to the second end of the tether, the trocar needle including:
       (i) a curved elongate body having an outer circumference, a distal end portion, a proximal end portion and an outer circumferential surface, said outer circumferential surface transitioning proximally to a recessed grip region at the proximal end portion, said recessed grip region having opposed surfaces recessed from the outer circumferential surface;
       (ii) a penetrating tip formed at the distal end portion of the body and at least one angled facet converging at the penetrating tip; and
       (iii) a notch formed at the distal end portion of the curved body immediately proximal the penetrating tip, the notch being defined by a surface extending between the outer circumferential surface and the at least one angled facet thereof, said notch configured for enhancing visualization, control and haptic perception by a surgeon when utilizing the needle.

11. The trocar needle assembly of claim 10, wherein the grip region formed at the proximal end portion of the body is configured to facilitate gripping by a surgical grasping device.

12. The trocar needle assembly of claim 10, wherein the elongate body is substantially circular in cross-section.

13. The trocar needle assembly of claim 10, wherein the elongate body is curved such that the proximal end portion and the distal end portion of the elongate body are oriented in respective directions which are substantially transverse relative to one another.

14. The trocar needle assembly of claim 13, wherein the elongate body is curved between 45 and 75 degrees.

15. The trocar needle assembly of claim 10, wherein the body is formed of a metal.

16. The trocar needle assembly of claim 15, wherein the body is formed of a stainless steel alloy.

17. The trocar needle assembly of claim 10, further including two or more angled facets converging at the penetrating tip.

18. The trocar needle assembly of claim 10, wherein the trocar needle is detachably engaged to the tether.

19. The trocar needle assembly of claim 11, wherein the grip region is formed at the proximal end portion of the body distal to an attachment portion.

* * * * *